US009775516B2

(12) United States Patent
Dziubinski

(10) Patent No.: US 9,775,516 B2
(45) Date of Patent: Oct. 3, 2017

(54) OUTPATIENT MONITORING SYSTEMS AND METHODS

(71) Applicant: Medicalgorithmics S.A., Warsaw (PL)

(72) Inventor: Marek Dziubinski, Warsaw (PL)

(73) Assignee: MEDICALGORITHMICS S.A., Warsaw (PL)

( * ) Notice: Subject to any disclaimer, the term of this patent is extended or adjusted under 35 U.S.C. 154(b) by 205 days.

(21) Appl. No.: 13/705,750

(22) Filed: Dec. 5, 2012

(65) Prior Publication Data

US 2013/0093602 A1 Apr. 18, 2013

Related U.S. Application Data

(63) Continuation of application No. 12/865,437, filed as application No. PCT/IB2009/007469 on Nov. 16, 2009, now Pat. No. 9,603,523.

(60) Provisional application No. 61/115,214, filed on Nov. 17, 2008, provisional application No. 61/236,602, filed on Aug. 25, 2009.

(51) Int. Cl.
*A61B 5/00* (2006.01)
*G06F 19/00* (2011.01)
*G06Q 50/22* (2012.01)
*H04L 29/08* (2006.01)

(52) U.S. Cl.
CPC .......... *A61B 5/0002* (2013.01); *A61B 5/0022* (2013.01); *A61B 5/72* (2013.01); *A61B 5/7475* (2013.01); *G06F 19/322* (2013.01); *G06F 19/3406* (2013.01); *G06F 19/3418* (2013.01); *G06Q 50/22* (2013.01); *H04L 67/10* (2013.01)

(58) Field of Classification Search
CPC .... A61B 5/0002; A61B 5/0022; G06F 19/322
USPC .......................................... 705/2–3; 600/300
See application file for complete search history.

(56) References Cited

U.S. PATENT DOCUMENTS

| | | |
|---|---|---|
| 5,657,398 A | 8/1997 | Guilak |
| 5,832,490 A | 11/1998 | Riley |
| 5,931,791 A | 8/1999 | Saltzstein et al. |
| 6,083,248 A | 7/2000 | Thompson |

(Continued)

FOREIGN PATENT DOCUMENTS

| | | |
|---|---|---|
| EP | 1637070 A2 | 3/2006 |
| WO | 02082984 A1 | 10/2002 |
| WO | 03019450 A2 | 3/2003 |

*Primary Examiner* — Christopher L Gilligan
(74) *Attorney, Agent, or Firm* — Brown Rudnick LLP; Nikhil Patel

(57) ABSTRACT

Described are computer-based methods and apparatuses, including computer program products, for outpatient monitoring. In some examples, the outpatient monitoring technology includes a system for remote monitoring and consultations of patients' state associated with automated interpretation of vital signs signals. In other examples, the outpatient monitoring technology includes a system for remote monitoring of patients' state associated with analysis of full-disclosure vital signs digital signals with reduced bit data or channel data. In some examples, the outpatient monitoring technology includes a system for remote monitoring of patients' state associated with ongoing automated analysis and transmission of full-disclosure vital signs digital signals and automatically generated signals' interpretation results and manually marked patient symptoms.

5 Claims, 7 Drawing Sheets

(56) References Cited

U.S. PATENT DOCUMENTS

| | | |
|---|---|---|
| 6,161,043 A | 12/2000 | McClure |
| 6,287,252 B1 | 9/2001 | Lugo |
| 6,336,871 B1 | 1/2002 | Ihara et al. |
| 6,366,871 B1 | 4/2002 | Geva |
| 6,416,471 B1 * | 7/2002 | Kumar et al. ............... 600/300 |
| 6,790,178 B1 | 9/2004 | Mault et al. |
| 6,936,007 B2 | 8/2005 | Quy |
| 6,970,737 B1 | 11/2005 | Brodnick et al. |
| 7,254,449 B2 | 8/2007 | Karunasiri |
| 7,286,880 B2 | 10/2007 | Olson et al. |
| 7,288,066 B2 | 10/2007 | Drew |
| 7,930,191 B1 | 4/2011 | Rogers |
| 7,945,457 B2 | 5/2011 | Zaleski |
| 8,112,149 B2 | 2/2012 | Sholder |
| 8,234,125 B2 | 7/2012 | Skocic |
| 8,249,894 B2 | 8/2012 | Brown |
| 8,255,238 B2 | 8/2012 | Powell et al. |
| 8,358,590 B2 | 1/2013 | Pekarske et al. |
| 8,483,807 B2 | 7/2013 | Kurzweil et al. |
| 8,682,692 B2 | 3/2014 | Morris |
| 2002/0198473 A1 | 12/2002 | Kumar |
| 2003/0065653 A1 * | 4/2003 | Overton et al. ............... 707/3 |
| 2004/0054760 A1 | 3/2004 | Ewing et al. |
| 2004/0073098 A1 | 4/2004 | Geva et al. |
| 2004/0093239 A1 | 5/2004 | Ott et al. |
| 2004/0122294 A1 | 6/2004 | Hatlestad et al. |
| 2006/0008058 A1 | 1/2006 | Dai et al. |
| 2006/0036134 A1 | 2/2006 | Tarassenko et al. |
| 2006/0094968 A1 | 5/2006 | Drew |
| 2006/0137699 A1 | 6/2006 | Moore et al. |
| 2006/0173267 A1 * | 8/2006 | Chiang et al. ............... 600/407 |
| 2007/0010721 A1 | 1/2007 | Chen et al. |
| 2007/0112275 A1 * | 5/2007 | Cooke ............... A61B 5/0456 600/513 |
| 2007/0149952 A1 | 6/2007 | Bland et al. |
| 2007/0253021 A1 | 11/2007 | Mehta et al. |
| 2007/0255120 A1 | 11/2007 | Rosnov |
| 2007/0265508 A1 | 11/2007 | Sheikhzadeh-Nadjar et al. |
| 2007/0276262 A1 | 11/2007 | Banet et al. |
| 2008/0018454 A1 | 1/2008 | Chan et al. |
| 2008/0045815 A1 | 2/2008 | Derchak et al. |
| 2008/0076973 A1 | 3/2008 | Muradia |
| 2008/0249376 A1 | 10/2008 | Zaleski |
| 2009/0070148 A1 * | 3/2009 | Skocic ............... 705/3 |
| 2010/0210953 A1 | 8/2010 | Sholder et al. |
| 2010/0222689 A1 | 9/2010 | Kurzweil et al. |
| 2011/0213620 A1 | 9/2011 | Dziubinski |
| 2012/0165629 A1 | 6/2012 | Merritt et al. |
| 2012/0172671 A1 | 7/2012 | Pekarske et al. |
| 2013/0013342 A1 | 1/2013 | Morris |
| 2013/0137937 A1 | 5/2013 | Dziubinski |

* cited by examiner

OUTPATIENT MONITORING SYSTEMS AND METHODS

RELATED APPLICATIONS

This application claims the benefit of U.S. Provisional Application No. 61/236,602, filed on Aug. 25, 2009, and U.S. Provisional Application No. 61/115,214, filed on Nov. 17, 2008, the entire teachings of the above applications are incorporated herein by reference.

BACKGROUND

Use of telemedicine can have a significant impact on individual health and can therefore favorably impact longevity. The value to the economy for these improvements in life expectancy is about as large as the value of all other consumption goods and services combined. In this regard, certain health services can be greatly enhanced via telemedicine. For example, home health services are receiving a great deal of attention and investment in many countries around the world. Telemedicine technologies enable home health providers to redefine patient treatment plans, as they are able to increase virtual patient visits through the elimination of a significant percentage of travel to patients' homes. In addition, in many situation outpatient monitoring allows for hospitalizations prediction, which results in actions leading to avoiding such expensive procedures. Further, access to quality, state of the art health care in underserved areas, such as rural communities, is one of the most important promised benefits of telemedicine. Rural residents are not second-class citizens; they deserve access to health care services that those in metropolitan areas enjoy.

An example of popular telemedicine applications are long-term, outpatient arrhythmia diagnostic systems, where patients are monitored for several weeks, while staying at home or carrying their normal lives. These systems utilize a concept of transmitting short ECG fragments, when an important cardiac event occurs. In more obsolete applications, the event transmissions are manually triggered by the patients, while most recent applications use intelligent algorithms, operating in real-time, which based on automatically detected events, trigger the transmissions. Both of the above applications can be viewed as so-called 'event systems', because they transmit only short ECG fragments, representing limited events only. Diagnostic reports from such systems usually contain limited, in terms of statistical representation, information describing the normal and abnormal heart rhythm and produce qualitative rather than quantitative results. On the contrary, the so called 'Holter systems', popular applications for short term (usually 24 hours or 48 hours) arrhythmia diagnostics, allow for reviewing the entire full-disclosure ECG signal and verifying classification results for each heart beat, hence they are capable of producing qualitative and comprehensive statistical reports, with each heart beat counted and classified. The 'Holter systems', however, are offline applications, where the ECG signal is stored by 'Holter recorders' carried by the patients, and after the diagnostic session is completed, the recorders are returned to a physician/specialist for data download and automated analysis and post-processing.

Thus, a need exists in the telemedicine field for outpatient monitoring systems and methods allowing for generating more quantitative analysis results.

FIELD OF THE INVENTION

The present invention relates generally to computer-based methods and apparatuses, including computer program products, for outpatient monitoring.

SUMMARY

One approach to outpatient monitoring is a system for remote monitoring and consultations of a patients' state associated with automated interpretation of vital signs signals. The system including at least one portable monitor, each portable monitor configured to: acquire data signals representative of a patient's vital signs; interpret the representative data signals; and generate interpretation result data; and transmit the interpretation results and the vital signs signals. The system further includes at least one monitoring computer station, the monitoring computer station including: a downloading module for obtaining the data signals representative of the patients' vital signs and the interpretation result data; a display module for viewing the obtained data signals representative of the patients' vital signs and the interpretation result data; a revision module for correcting and/or affixing comments to the interpretation result data; and a synchronization module for synchronizing the revised interpretation result data with a data interpretation center and repository.

Another approach to outpatient monitoring is a system for remote monitoring of patients' state associated with analysis and transmission of full-disclosure data signals having reduced bit data and/or reduced number of channels, representative of patient's vital signs. The system includes at least one portable monitor configured to acquire, store and compress/reduce data signals representative of patients' vital signs with a lossy compression/bit reduction algorithm/channel reduction procedure; and transmit the compressed data signals along with some uncompressed vital signs signal data fragments. The system further includes at least one monitoring computer station, the monitoring computer station including a downloading module for obtaining the compressed/reduced data signals and the uncompressed/unreduced data fragments; and a verification module visually distinguishing between the compressed/reduced data signals and the uncompressed/unreduced data fragments.

Another approach to outpatient monitoring is a system for remote monitoring of a patients' state associated with ongoing automated analysis and transmission of full-disclosure data signals representative of vital signs, interpretation results data, and manually marked patient symptoms information data. The system including at least one portable patient monitor, the portable patient monitor including an acquisition module for acquiring digital data signals representative of full-disclosure vital signs; an analysis module for interpreting the acquired digital data signals; an interactive user interface for reporting subjective symptoms; a recording module for storing the full-disclosure data signals representative of vital signs, the interpretation results, and the information entered via the user interface; and a transmission module configured to transmit the data signals representative of full-disclosure vital signs, the interpretation results, and the information entered via the user interface.

Another approach to outpatient monitoring is a method for remote monitoring of patients' state associated with interpretation results data representative of the patients' vital signs. The method including the steps of remotely initializing at least one monitoring session having an associated unique identification number; obtaining the sessions' identification number; associating a patients' personal data and a consultants' personal data with the obtained sessions' identification number; transmitting vital signs signals with interpretation results; verifying the interpretation results data and/or post-processing the received signals data and/or inserting comments to the interpretation results data; and synchronizing the verified or commented on interpretation results data with a data interpretation center and repository.

Another approach to outpatient monitoring is a method for remote monitoring of a patients' state associated with analysis of full-disclosure data signals representative of vital signs having a reduced bit data/reduced number of channels. The method including the steps of receiving bit-reduced and/or channel-reduced full-disclosure signals data representative of a patients' vital signs and uncompressed/unreduced data signals fragments; visually reviewing the compressed/reduced full-disclosure signals data representative of a patients' vital signs and the uncompressed data signals fragments; and remotely requesting additional uncompressed/unreduced data signals fragments for a more detailed analysis and/or verification.

Another approach to outpatient monitoring is a method for remote monitoring of a patients' state associated with ongoing automated analysis and transmission of full-disclosure signals data representative of a patients' vital signs, automatically generated interpretation data results, and manually marked patient symptoms information. The method including the steps of receiving, in a remote location, data representative of a patients' full-disclosure signals with interpretation data results and manually marked subjective symptoms information; reviewing, from the remote location, the data representative of a patients' full-disclosure signals with the interpretation data results and the manually marked subjective symptoms information; and reporting, from the remote location, the interpretation data results and the manually marked subjective patient symptoms information.

Another approach to outpatient monitoring is a computer program product, tangibly embodied in an information carrier, the computer program product including instructions being operable to cause a data processing apparatus to perform any one of the approaches and/or examples described herein.

Another approach to outpatient monitoring is a system for remote monitoring and consultations of a patients' state associated with automated interpretation of vital signs signals. The system including at least one means for portable monitoring, each means for portable monitoring configured to acquire data signals representative of a patient's vital signs; interpret the representative data signals; and generate interpretation result data; and transmit the interpretation results and the vital signs signals. The system further including at least one monitoring computer station, the monitoring computer station including means for obtaining the data signals representative of the patients' vital signs and the interpretation result data; means for viewing the obtained data signals representative of the patients' vital signs and the interpretation result data; means for correcting and/or affixing comments to the interpretation result data; and means for synchronizing the revised interpretation result data with a data interpretation center and repository.

Another approach to outpatient monitoring is a system for remote monitoring of patients' state associated with analysis and transmission of full-disclosure data signals having reduced bit data and/or reduced number of channels, representative of patient's vital signs. The system including at least one means for portable monitoring configured to acquire, store and compress data signals representative of patients' vital signs with a lossy compression/bit reduction algorithm/channel reduction procedure; and transmit the compressed/reduced data signals along with some uncompressed/unreduced vital signs signal data fragments. The system further including at least one means for monitoring, the means for monitoring including: means for obtaining the compressed data signals and the uncompressed/unreduced data fragments; and means for visually distinguishing between the compressed/reduced data signals and the uncompressed/unreduced data fragments.

Another approach to outpatient monitoring is a system for remote monitoring of a patients' state associated with ongoing automated analysis and transmission of full-disclosure data signals representative of vital signs, interpretation results data, and manually marked patient symptoms information data. The system including at least one means for portable patient monitoring, the means for portable patient monitoring including means for acquiring digital data signals representative of full-disclosure vital signs; means for interpreting the acquired digital data signals; means for reporting subjective symptoms; defining symptom's characteristics; and defining patient's activity and circumstances related to the symptom's occurrence; means for storing the full-disclosure data signals representative of vital signs, the interpretation results, and the information entered via the user interface; and means for transmitting the data signals representative of full-disclosure vital signs, the interpretation results, and the information entered via the user interface.

In other examples, any of the approaches above can include one or more of the following features.

In some examples, the portable monitor operates in real-time and continually generates the data signals representative of the patients' vital signs, the interpretation result data, and a hardware status data of the at least one portable monitor.

In other examples, the hardware status data contains information describing the portable monitor's battery status, memory status and mobile telephony communication error list.

In some examples, the data interpretation center and repository receives the data files from the at least one portable monitor, reads the data signals representative of the patients' vital signs and inserts the interpretation result data, with links to the data signals representative of the patients' vital signs, into the data repository.

In other examples, the at least one monitoring computer stations synchronizes remotely with the data interpretation center and repository.

In some examples, the revised interpretation result data are propagated to the data interpretation center and repository and distributed further to the at least one monitoring computer station connected with the data interpretation center and repository.

In other examples, the at least one portable monitor selects the uncompressed/unreduced data fragments based on generated interpretation results and/or a signal condition representing at least one significant signal event.

In some examples, the verification module of the at least one monitoring computer station remotely requests additional uncompressed/unreduced data fragments stored in the at least one portable monitor's memory for additional review.

In other examples, the additionally requested uncompressed/unreduced data fragments and the compressed/reduced data signals are visually distinguished by the at least one monitoring computer station with the use of the verification module.

In some examples, the at least one portable patient monitor triggers the data transmission based on the interpretation results, the patient's interaction, or on a periodic schedule.

In other examples, the interactive user interface allows for defining symptom's characteristics; and defining patient's activity and circumstances related to the symptom's occurrence.

In other examples, the sessions' identification number is a combination of the session initialization time, date, and a portable monitor's identification number.

In some examples, the method further including creating an event list based on interpretation results data, each event having an unconfirmed status indicator.

In other examples, the method further including changing the unconfirmed status indicator to a confirmed status indicator when the event has been detected properly, deleted, determined to be a false event, determined to be unclear, or when the consultant is not sure whether it is a true event or an incorrectly detected event.

In some examples, the method further including correlating interpretation data results with the manually marked, subjective patient symptoms information.

In other examples, the method further including generating monitoring reports including the interpretation data results correlated with the manually marked subjective patient symptoms information.

In some examples, the monitoring reports are generated on an ongoing basis, during the patient monitoring, and at the end of the monitoring session.

An advantage to the outpatient monitoring technology quantitative analysis results can be generated by accessing remotely the full-disclosure signals, thereby enabling detailed post-processing of the data, detailed verification of the analysis results, and more confidence in generating qualitative analysis reports.

Other aspects and advantages of the present invention will become apparent from the following detailed description, taken in conjunction with the accompanying drawings, illustrating the principles of the invention by way of example only.

BRIEF DESCRIPTION OF THE DRAWINGS

The foregoing and other objects, features and advantages will be apparent from the following more particular description of embodiments, as illustrated in the accompanying drawings in which like reference characters refer to the same parts throughout the different views. The drawings are not necessarily to scale, emphasis instead being placed upon illustrating the principles of the embodiments.

DESCRIPTION

Figure 1:
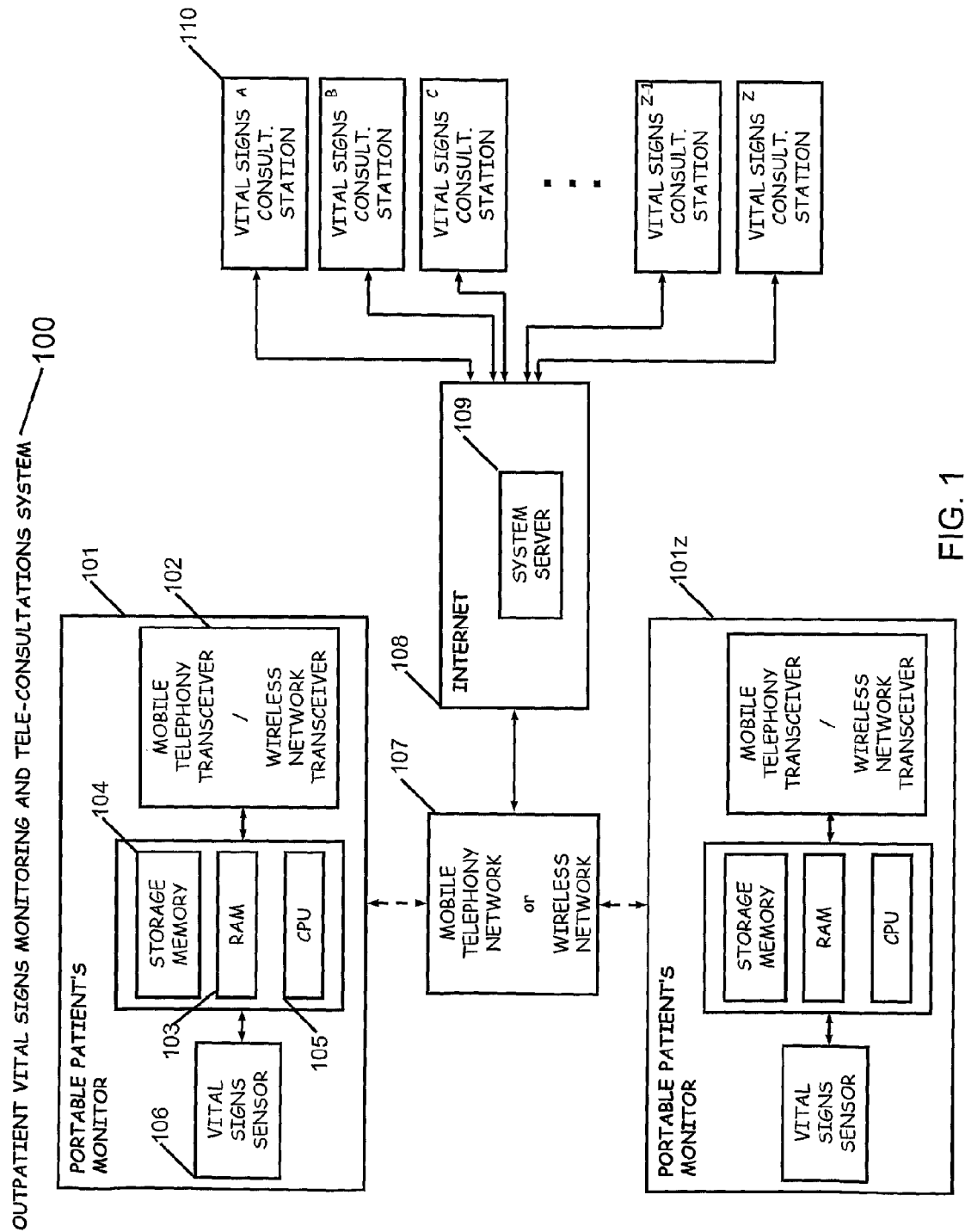
FIG. 1 is an illustration of vital signs signals outpatient monitoring and tele-consultations system.

Outpatient monitoring technology can include a system enabling long-term, outpatient and real-time analysis of vital signs signals, where the data is transmitted via a bandwidth-limited communication channel, such as mobile telephony network, during the diagnostic session on an ongoing basis. The outpatient monitoring technology can have the benefit of access to full-disclosure signals. The technology enables generation of more comprehensive and qualitative statistical analysis results on an ongoing basis and real-time response to the automatically detected events requiring immediate reaction, or to the symptomatic events reported by the patients during the monitoring. The technology also allows for correlating the symptomatic events, reported by the patients, with the full-disclosure vital signs signals and the automatically generated signal description.

The outpatient monitoring technology can include a system for outpatient monitoring of patients' status, based on automated analysis of vital signs signals. The vital signs signals can be acquired through a sensor in a portable patients' monitor. The portable monitor can analyze the signals in real-time and can generate vital signs interpretation information including, for example, information for emergency cases. Based on the interpretation results, significant events associated with patient state are detected. In addition, the acquired vital signs signals are compressed/downsized with lossy-compression/bit-reduction or channel-reduction algorithm which generally decreases quality of the vital signs signals, or reduces information contained by the signals, but enables transmission of the continuous, full-disclosure signals through a bandwidth-limited communication channel (e.g., mobile telephony network, wired telephony network, etc.) to a specialist at a remote location. In addition, based on the automated interpretation results, i.e., in accordance to the determined events, short, uncompressed/unreduced vital signs signals fragments are selected. The full-disclosure, lossy-compressed/bit-reduced, or channel-reduced signals along with the selected uncompressed/unreduced fragments and the interpretation results can be stored in digital files and transmitted via the bandwidth-limited communication channel, with the use of any type of transmission mechanism, e.g., file transfer protocol to a remote system server connected to the internet. The entire vital signs signals can be stored in the portable patients' monitor in an uncompressed/unreduced format for later reference. When a new monitoring session is initiated with the use of the portable patient's monitor, a session unique ID number can be generated and/or can be stored in the session's initialization digital file. The ID number can be a combination of the initialization time and date and the device unique ID number. The system server can receive the data files and can insert the interpretation results with links to the transmitted data files to a database. Once the server detects a new monitoring session ID file, the server can create a new folder for storing the session digital files, and can create a new record in the database. The vital signs signals monitoring computer stations can have access to a network (e.g., internet, local area network, etc.), and can connect remotely to the system server and the database, can download the monitoring digital files, and/or can display information about the newly initiated session. When the new session is detected by the monitoring center's consultants with the use of the monitoring computer stations, the monitoring center's representative contacts the portable monitor's owner/user, e.g., a physician or a patient in remote location, and obtains personal data, medical history and other information regarding the monitored person and inserts it to the system server's database. The information can be also inserted directly to the system server's database, by the owner/user of the portable monitor, via a web browser, through a web based interface.

In some examples, personal data of all consultants responsible for analyzing the patient's vital signs signals during the monitoring session and personal information of the user/owner of the portable monitor who initiated the monitoring session from remote location can be inserted to the system server's database and can be associated with the monitoring session's record. The vital signs monitoring computer stations databases can synchronize with the system server database and can download the monitoring session data files. The consultants can review the full-disclosure vital signs signals with the attached interpretation information in order to verify the automated analysis results. The consultants can post-process the received full-disclosure signals in order to generate more complete statistical reports. All events, automatically detected by the portable patients' monitor and/or events generated during the post-processing procedure can have the initial status set to "unconfirmed". The operators can verify and review the events. The operators can change the status to "confirmed" if the event has been detected properly. The operators can change the status to "deleted" in case of false events. The operators can change the status to "unclear", in case of doubts, so other operators can consult the event.

In other examples, the consultants can modify events description and/or insert comments or impressions. All the status modifications and/or changes and/or inserted information are propagated through the system server to all other vital signs monitoring stations instantly or nearly instantly. The monitoring stations can also display the full-disclosure vital signs signals with different color than the uncompressed/unreduced vital signs signals fragments. Therefore the operators/consultants, aware of the lossy-compressed/bit-reduced or channel-reduced signals limitations, can remotely request from the portable patients' monitors, additional uncompressed/unreduced vital signs signals fragments for verification, in case of significant events that were not automatically selected for representation with the uncompressed/unreduced data. Any fragment of the full-disclosure vital signs can be requested, since the entire uncompressed/unreduced vital signs representation signals are stored in the portable monitor's memory.

The technology can include a system for outpatient monitoring of patients' status, based on automated analysis of vital signs signals and subjectively indicated symptoms, marked by the patient with the use of interactive interface of the patient's monitor, allowing for correlation of the objectively detected events and/or the subjective events. The vital signs signals can be acquired through a sensor by a portable patients' monitor. The portable monitor can analyze the signals in real-time and can generate vital signs signals interpretation information. Based on the interpretation results significant/emergency events associated with patient state are detected. In addition, the patient, with the use of an interactive interface of the portable patient monitor, can indicate that he/she felt symptom or symptoms. The patient and/or the operator can determine additional information related to the symptoms occurrence, such as patient's activity when the symptom happened, and/or the type of felt symptom or symptoms.

The full-disclosure signals along with the additional data including interpretation results and the patient reported symptoms can be stored in digital files and transmitted via a bandwidth-limited communication channel (e.g. mobile telephony network) with the use of any type of transmission mechanism, e.g., file transfer protocol to a system server connected to the Internet. The entire vital signs signals with the additional data are stored in the portable patients' monitor for later reference and remote or direct retrieval.

In other examples, the patient monitor provides interactive tools for real-time symptomatic events reporting, enabling for synchronization of the felt symptoms with symptoms represented in the vital signs signals and the signals annotations.

The outpatient vital signs signals monitoring system can utilize any type of network (e.g. a mobile telephony network, other bandwidth-limited communication network, etc.) advantageously enabling for data exchange between a patient's monitor at a patient's location and a physician/specialist from a remote location.

In some examples, the system transmits lossy-compressed/bit-reduced or channel-reduced full-disclosure signals representation and enables remote consultations and verification and post-processing of the automatically generated interpretation results and the full-disclosure signals. The system, despite bandwidth limitation of the wireless network transmission channel, can enable access to the full-disclosure signals representations with interpretation results from remote location due to utilizing lossy compression/bit reduction algorithm, or channel reduction approach. The system, with the use of a portable patient's monitor which is a microcomputer with built in wireless network communication module, can automatically interpret the vital signs signals in real-time, stores the results in memory and transmits the interpretation results, along with the signals, to the remote system server.

In other examples, the transmitted lossy-compressed/bit-reduced or channel-reduced representation signals are accompanied by a limited number of uncompressed/unreduced signals fragments, representing significant signals events. The plurality of remote monitoring computer stations, in connection with the system server thought a network (e.g., internet, wide area network, etc.), can download and/or can visualize the signals and the interpretation results. The monitoring computer stations, operated by consultants, can modify and/or change the automatically generated vital signs interpretation results and post-process and post-analyze the full-disclosure signals and/or allow for inserting additional comments or impressions. The inserted information and/or the modifications are propagated through the system server to other monitoring computer stations. Such information exchange can be viewed as consultations between the monitoring computer stations' operators. The operators, after initial review of the lossy-compressed/bit-reduced/channel-reduced full-disclosure vital signs signals can remotely request, from the portable patient monitors' memory, additional uncompressed/unreduced vital signs signals fragments for more thorough analysis and/or verification.

In some examples, the system transmits full-disclosure signals with automatically generated signals' description and information related to subjective symptoms marked by the patient, allowing for correlation and reporting of the automatically detected and manually marked events.

In other examples, the system, with the use of a portable patient's monitor, which is a microcomputer with built in mobile telephony or wireless network communication module, automatically interprets the vital signs signals in real-time, can store the results in memory and can transmit, on an ongoing basis, the interpretation results for emergency events, along with the signals and information related to the subjective symptoms, to a remote monitoring center. The patient, with the use of interactive user interface of the portable patient monitor, can manually report subjective symptoms with indication of the symptoms characteristics and information describing patient's activity during which, or circumstances under which the felt symptoms occurred.

FIG. 1 is an illustration of the system 100 diagram for providing remote outpatient real-time vital signs signals monitoring with the capability of tele-consultations between the system operators/specialists operating the vital signs data reviewing and tele-consultation stations 110A, B, C through Z–1 and Z, being connected to the system server 109 (e.g., directly via a network, indirectly via a network, etc.). The patient's portable monitor 101 transmits the data, through a network 107 (e.g., a mobile telephony network, a wireless network, etc.) and/or through the Internet 108 to the system server 109. The other patients' portable monitors 101 through 101z transmit the data to the system server 109. The system 100 includes, but is not limited to, the following components:

1) Portable monitor 101—a microcomputer connected to a vital signs signals sensor 106 with built in wireless network transceiver (e.g., a global system for mobile communication (GSM) module) 102, central processing unit (CPU) 105 for data processing, random access memory (RAM) 103 and storage memory 104 for storing the signals and processing results with the use set of programmed instructions for real-time vital signs signals interpretation, compression and communication management.
2) Vital signs signals data reviewing, post-processing and tele-consultation station 110—monitoring computer station with software for data downloading, storing and propagating the inserted and generated, by the operator, additional analysis results, and results modifications and other inserted information related to the diagnostic session from the operated monitoring computer station to all other monitoring computer stations assigned to the diagnostic session, through the system server.
3) System server 109 with software for communication management between the patients' monitors and the vital signs data reviewing and tele-consultation stations and distributing the inserted information between the vital signs data reviewing and tele-consultation station.

When the portable monitor based software detects pathological/emergency events, the software can automatically select and send uncompressed/unreduced vital signs signals strips representing these events, along with the lossy-compressed/bit-reduced/channel reduced full-disclosure signal segment and the interpretation results representing this segment. The interpretation results and the full-disclosure signal segments can be, for example, streamed to the system server in short time intervals.

Figure 2:
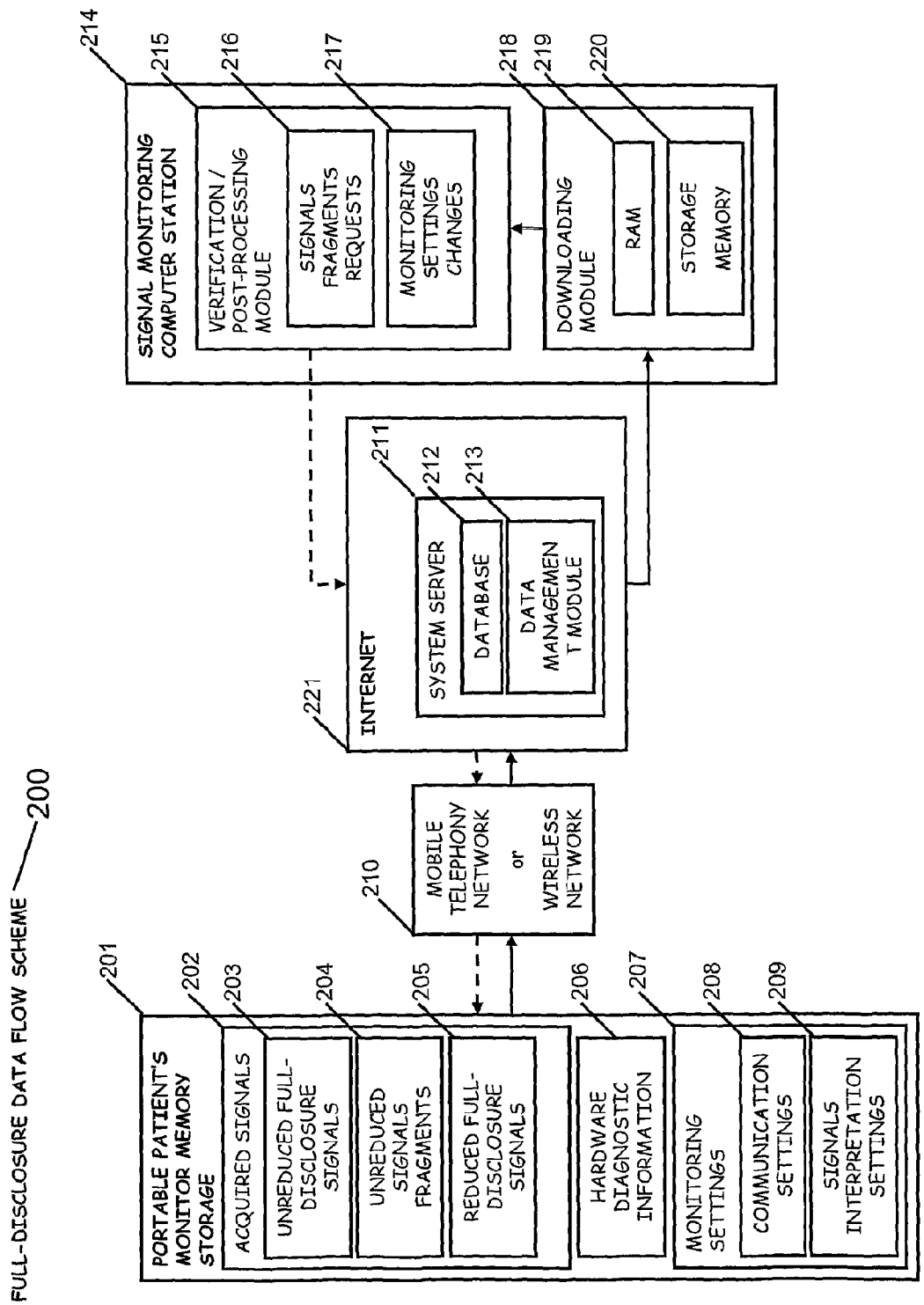
FIG. 2 schematically illustrates full-disclosure signal data flow.

FIG. 2 is an illustration of the full-disclosure data flow scheme 200 between the portable monitor 201 and the vital signs data reviewing, post-processing and tele-consultation station, i.e. the vital signs signals monitoring computer station 214. The vital signs signal data is transmitted through the mobile telephony or other wireless network 210 and further through the Internet 221 to the system server 211. The scheme includes, but is not limited to, the following components:

1) Portable monitor 201—a microcomputer with memory for storing the vital signs signals 202 in the following forms: full-disclosure uncompressed/unreduced signals representation 203, full-disclosure lossy-compressed/bit-reduced/channel-reduced signals representation 205, uncompressed/unreduced signals fragments 204 representing significant signal events; hardware diagnostic information 206 including memory status information and communication errors list; monitoring settings 207 information, including communication settings 208 with server IP and port number and signals analysis settings 209 with the analysis parameters and thresholds.
2) System server 211—including database 212 and the data management module 213 for exchanging information between the portable monitors 201 and the monitoring computer stations 214.
3) Monitoring computer station with software 214—including the downloading module 218 with RAM 219 and storage memory 220 for vital signs signals download operations (e.g., obtaining the data signals representative of the patients' vital signs) and storing, the verification module 215 for reviewing and requesting uncompressed/unreduced signals strips 216 from the remote portable patient's monitor, and for modifying the portable patient's monitor settings 217.

In some examples, the portable monitor 201 acquires data signals representative of patients' vital signs, interprets the representative data signals, and generates interpretation result data based on the same.

In other examples, the portable monitor 201 operates in real-time and continuously generates the data signals representative of the patients' vital signs, the interpretation result data, and/or a hardware status data of the portable monitor 201. The hardware status data can include information describing the portable monitor's battery status (e.g., 80%, five minutes until battery failure, etc.), memory status (e.g., 90% memory capacity, four megabytes available, etc.), and/or a mobile telephony communication error list (e.g., 80% communication failure rate, five packets transmission attempts, or four packets lost in the past sixty seconds, etc.).

In other examples, the monitoring computer station includes a display module (not shown), a revision module (not shown), and/or a synchronization module (not shown). The display module enables viewing of the data signals representative of the patients' vital signs. The revision module enables the correcting and/or affixing comments to the interpretation result data. The synchronization module enables synchronizing the revised interpretation result and post-processing results data with a data interpretation center and repository (e.g., off-site data storage facility, etc.). The synchronization between the monitoring computer station and the data interpretation center and repository can occur remotely. The synchronization between the monitoring computer station and the data interpretation center and repository can occur based on revised interpretation result data and/or interpretation data generated during post-processing and/or any other condition.

Figure 3:
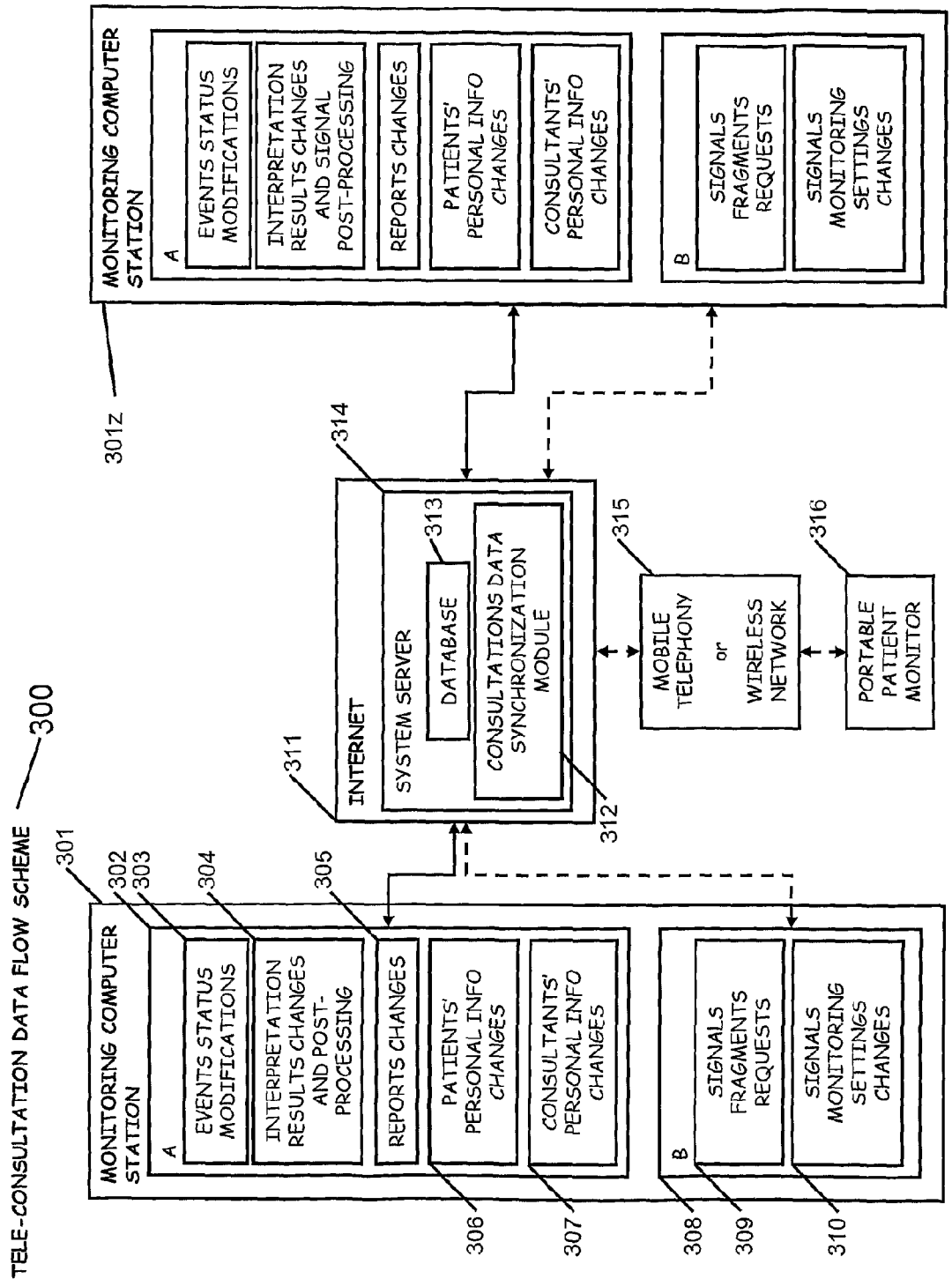
FIG. 3 schematically illustrates tele-consultations data flow.

FIG. 3 is an illustration of the tele-consultations data flow scheme 300 between the monitoring computer stations 301 through 301z and the portable patient's monitors 316 through the mobile telephony or wireless network 315 and further through the Internet 311. The scheme includes, but is not limited to, the following components:

1) Monitoring computer station 301 exchanging two sets of data:
   Data set A 302 exchanged only between the computer stations including:
      events status modifications 303,
      interpretation results changes 304,
      analysis reports changes 305,
      patients' personal info changes 306,
      consultants' personal info changes 307;
   Data set B 308 exchanged between the computer stations 301 and the portable monitor 316, including:
      information regarding the requested uncompressed signals fragments 309,
      signals monitoring settings changes 310;
2) System server 314—including database 313 and consultations data synchronization module 312 for exchanging information from data set B 308 between the monitoring computer stations 301 and the portable patient's monitors 316, and for synchronizing/exchanging information from data sets A 302 and B 308 between the operated monitoring computer station 301 all other monitoring computer stations 301 assigned to the same diagnostic session.
3) Portable patient monitor 316 receiving and responding to the uncompressed signals fragments requests and the signals interpretation settings changes from data set B 308.

Figure 4:
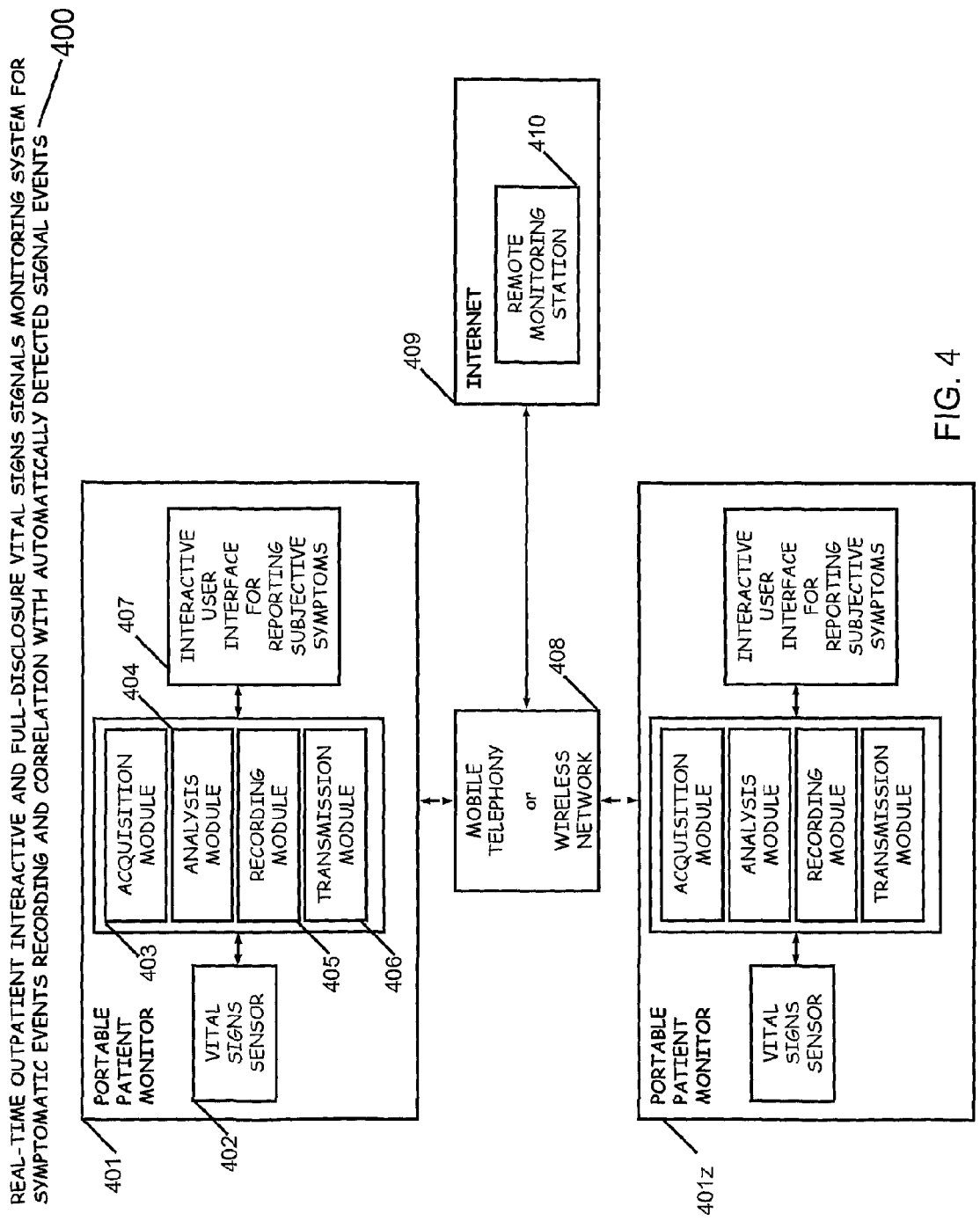
FIG. 4 is an illustration of the real-time outpatient interactive and full-disclosure vital signs signals monitoring system for symptomatic events recording and correlation with automatically detected signal events.

FIG. 4 is an illustration of real-time outpatient interactive and full-disclosure vital signs signals monitoring system for symptomatic events recording and correlation with automatically detected signal events 400. The system scheme includes, but is not limited to, the following components: portable patient monitors 401 through 401z, each including vital signs signals sensor 402, acquisition module 403 for vital signs signals acquisition, signal analysis module 404 for automatic signals interpretation, interactive user interface for reporting subjective symptoms 407 felt by the patient, recording module 405 for storing interactive interface operations introduced by the patient and transmission module 406 for transmitting the vital signs signals, the interpretation results and the manually triggered symptomatic events information through the mobile telephony or wireless network 408 and further through the Internet 409 to the remote monitoring stations 410, operated by trained specialists, responsible for reviewing the signals, verifying the automatically generated interpretation results, post-processing the full-disclosure signals and for generating diagnostic reports during and after the diagnostic session.

The systems, stations, monitors, and/or components described herein can, for example, utilize the CPU to execute computer executable instructions and/or include a processor to execute computer executable instructions (e.g., an encryption processing unit, a field programmable gate array processing unit, etc.). It should be understood that the systems, stations, and/or monitors can include, for example, other modules, devices, and/or processors known in the art and/or varieties of the illustrated modules, devices, and/or processors.

Figure 5:
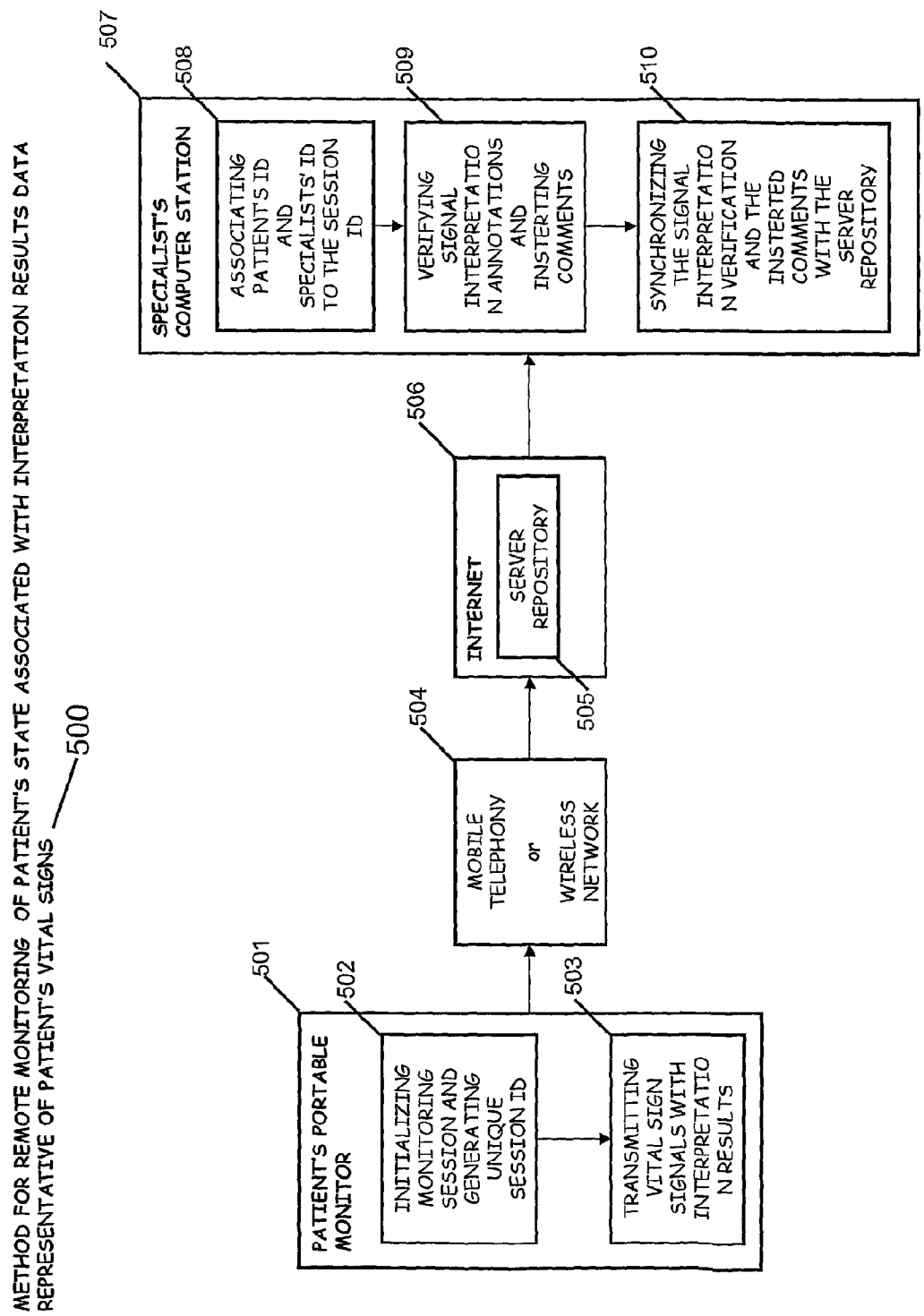
FIG. 5 is a flowchart illustration of a method for remote monitoring of patient's state associated with interpretation results data representative of patients' vital signs.

FIG. 5 is a flowchart 500 illustration of a method for remote monitoring of patient's state associated with interpretation results data representative of patients' vital signs. The method includes, but is not limited to, the following steps:
1) Initializing of the monitoring session 502 through the portable patient's monitor 501 interface;
2) Transmitting of the vital signs signals and the automatically generated interpretation results 503 to a remote location, through a bandwidth-limited communication channel 504, to the system server 505, accessible via Internet 506;
3) Associating of the initialized monitoring session ID with the patient's personal data and with the trained specialist's personal data 508 with the use of the specialist's computer station 507;
4) Verifying of the automatically generated signal interpretation results 509, including post-processing of the signal and inserting additional comments, related to the interpretation; and
5) Synchronizing of the post-processing interpretation modifications and the inserted comments with the server repository 510.

Figure 6:
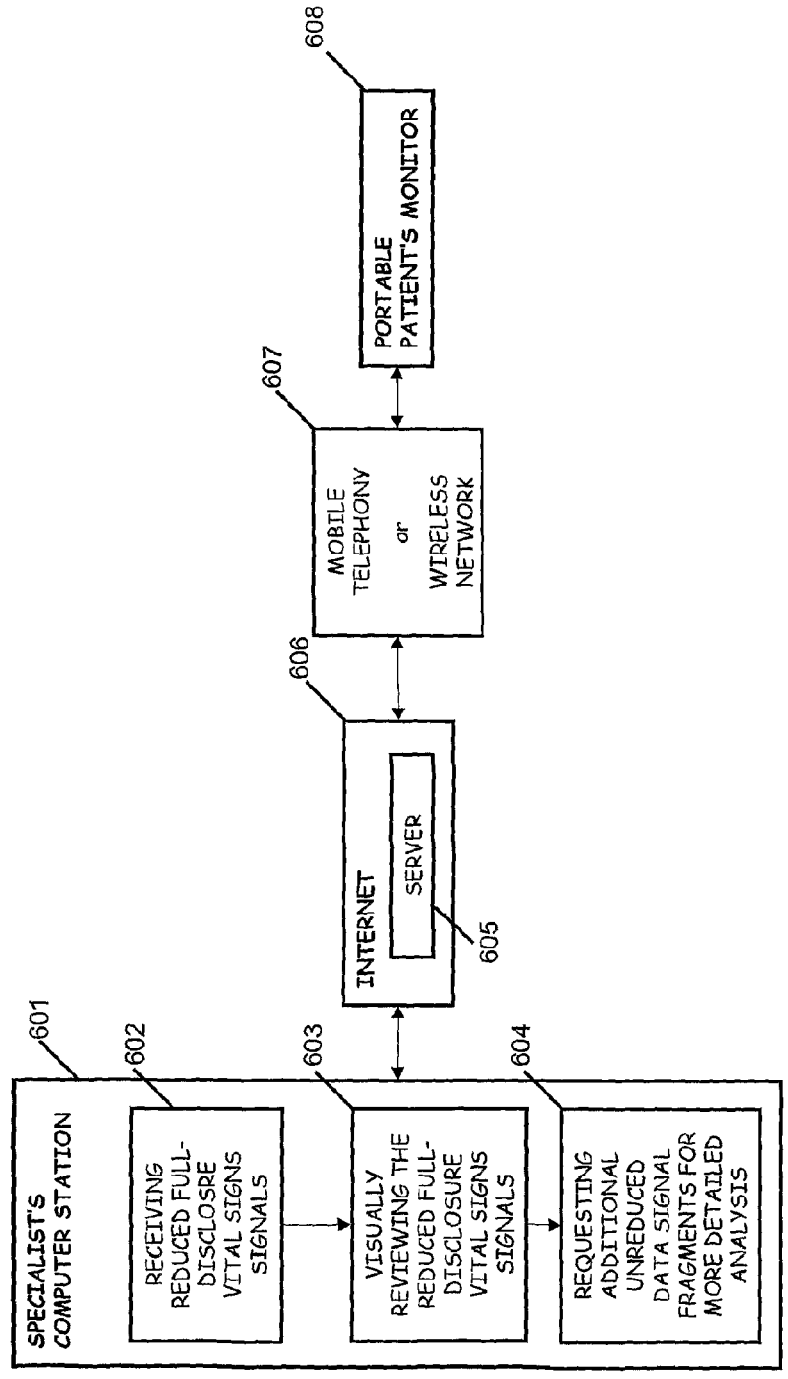
FIG. 6 is a flowchart illustration of a method for remote monitoring of patients' state associated with analysis of lossy-compressed/bit-reduced/channel-reduced full-disclosure vital signs signals.
Figure 7:
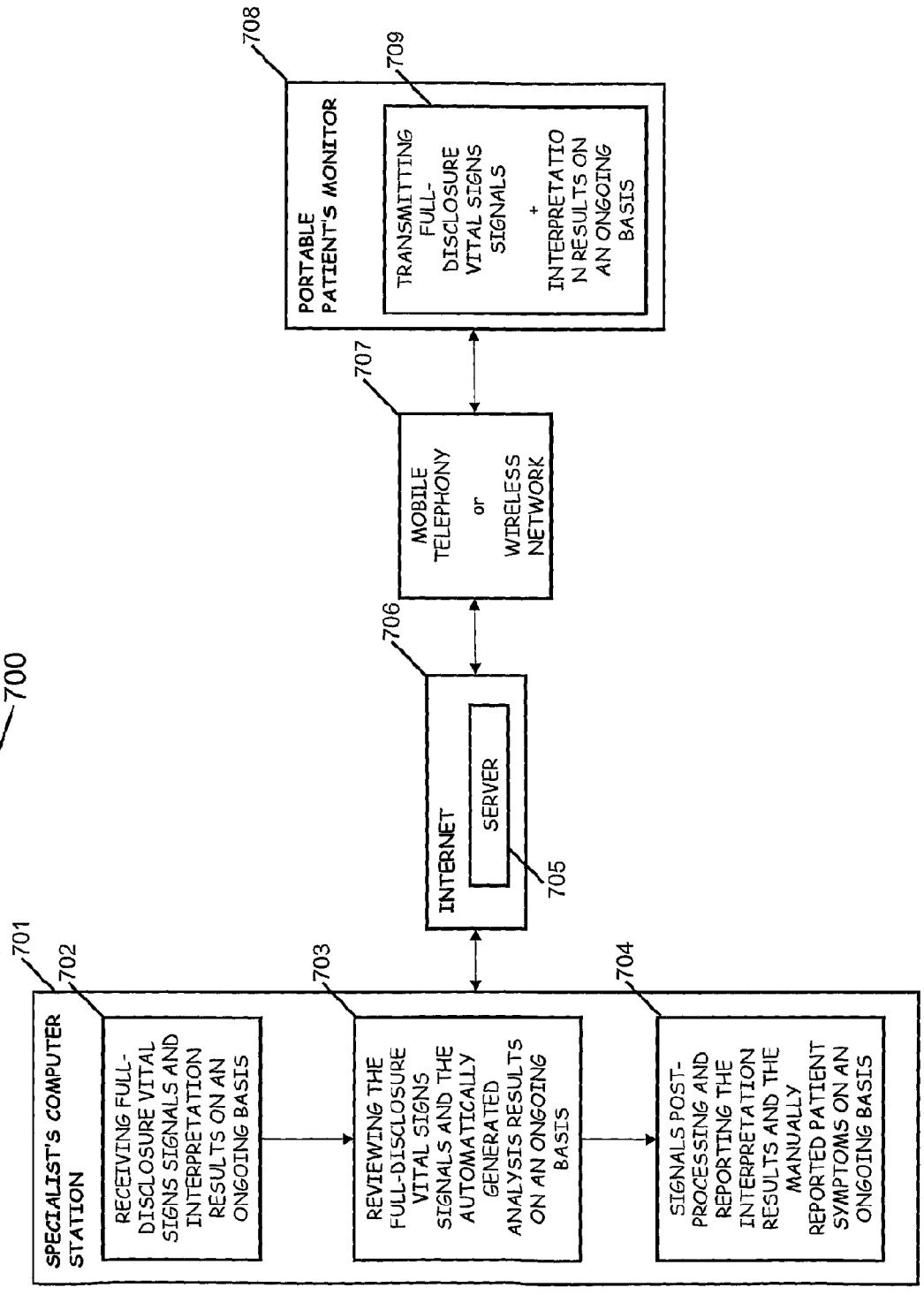
FIG. 7 is a flowchart illustration of a method for remote and real-time monitoring of patient's state associated with analysis of full-disclosure vital signs signals.

FIG. 6 is a flowchart 600 illustration of a method for remote monitoring of patients' state associated with analysis lossy-compressed/bit-reduced/channel-reduced full-disclosure vital signs signals. The method includes, but is not limited to the following steps:
1) Receiving a lossy-compressed and/or bit-reduced and/or channel-reduced full-disclosure signals data representative of patient's vital signs 602 from the portable patient's monitor 608, through a bandwidth-limited communication channel 607, via the system server 606 accessible through the Internet 605;
2) Visually reviewing the lossy-compressed/bit-reduced/channel-reduced full-disclosure vital signs signals 603 with the use of the specialist's computer station 601; and
3) Remotely requesting additional uncompressed/unreduced signals fragments, representing significant signal events, for verification and more detailed analysis and signal measurements 604 from the patient's monitor 608, through the bandwidth-limited communication channel 607, via the system server 606 accessible through the Internet 605;

FIG. 7 is a flowchart 700 illustration of a method for remote and real-time monitoring of patient's state associated with analysis of full-disclosure vital signs signals. The method includes, but is not limited to the following steps:
1) Receiving at remote location full-disclosure vital signs signals with the automatically generated interpretation results 702, from the portable patient's monitor 708, through a bandwidth-limited communication channel, via the system server 705 accessible through the Internet 706, on an ongoing basis during the monitoring;
2) Reviewing 703, with the use of specialist's computer station 701, the full-disclosure vital signs signals and the automatically generated analysis results on an ongoing basis, during the monitoring, and
3) Post-processing of the received full-disclosure signals, with the use specialist's computer station 701, in order to generate more detailed/more accurate interpretation results and reporting the results and the manually indicated patient's symptoms on an ongoing basis, during the monitoring 704.

In other examples, the portable patient's monitor 708 transmits 709 the remote location full-disclosure vital signs signals with the automatically generated interpretation results to the specialist's computer station 701 through a bandwidth-limited communication channel, via the system server 705 accessible through the Internet 706.

The above-described systems and methods can be implemented in digital, electronic circuitry, in computer hardware, firmware, and/or software. The implementation can be as a computer program product (i.e., a computer program tangibly embodied in an information carrier). The implementation can, for example, be in a machine-readable storage device and/or in a propagated signal, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Modules, subroutines, and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), 802.11 network, 802.16 network, general packet radio service (GPRS) network, Hiper-LAN), and/or other packet-based networks. Circuit-based networks can include, for example, the public switched telephone network (PSTN), a private branch exchange (PBX), a wireless network (e.g., RAN, bluetooth, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a world wide web browser (e.g., Microsoft® Internet Explorer® available from Microsoft Corporation, Mozilla® Firefox available from Mozilla Corporation). The mobile computing device includes, for example, a Blackberry®.

Comprise, include, and/or plural forms of each are open ended and include the listed parts and can include additional parts that are not listed. And/or is open ended and includes one or more of the listed parts and combinations of the listed parts.

One skilled in the art will realize the invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims, rather than by the foregoing description, and all changes that come within the meaning and range of equivalency of the claims are therefore intended to be embraced therein.

What is claimed is:

1. A method for remote monitoring of patients' state associated with interpretation results data representative of the patients' vital signs, comprising the steps of:
    remotely initializing a portable patient monitor to begin a monitoring session having an associated unique identification number, the remote initialization causing the portable patient monitor to acquire, via a vital signs sensor, continuous full-disclosure vital signs;

analyzing, in real time via the portable patient monitor, the continuous full-disclosure vital signs to identify at least one of: a pathological event and emergency event;

selecting, via the portable patient monitor, portions of the continuous full-disclosure vital signs to be stored, at the portable patient monitor, as uncompressed/unreduced data fragments based on generated interpretation results and/or a signal condition representing at least one significant signal event;

transmitting data signals representative of the continuous full-disclosure vital signs with interpretation results to a remote location, wherein the full-disclosure vital signs are real-time patient vital signs, by creating, at the portable patient monitor, data signals that includes a combination of bit-reduced/channel-reduced data signals and the uncompressed/unreduced data signals, wherein the uncompressed/unreduced data signals represent at least one of: the pathological event and emergency event; and synchronizing verified interpretation results data with a data interpretation center and repository of a remote monitoring station.

2. The method of claim 1, wherein the sessions' identification number is a combination of the session initialization time, date, and a portable monitor's identification number.

3. The method of claim 1, further comprising creating an event list based on interpretation results data, each event having an unconfirmed status indicator by the one or more processors.

4. The method of claim 3, further comprising changing the unconfirmed status indicator to a confirmed status indicator when the event has been detected properly, deleted, determined to be a false event, determined to be unclear, or when the consultant is not sure whether it is a true event or an incorrectly detected event by the one or more processors.

5. A non-transitory computer program product, tangibly embodied in a non-transitory information carrier, the computer program product including instructions being operable to cause a data processing apparatus to:

remotely initialize a portable patient monitor to begin a monitoring session having an associated unique identification number, the remote initialization causing the portable patient monitor to acquire, via a vital signs sensor, continuous full-disclosure vital signs;

analyze, in real time via the portable patient monitor, the continuous full-disclosure vital signs to identify at least one of: a pathological event and emergency event;

select, via the portable patient monitor, portions of the continuous full-disclosure vital signs to be stored, at the portable patient monitor, as uncompressed/unreduced data fragments based on generated interpretation results and/or a signal condition representing at least one significant signal event;

transmit data signals representative of the continuous full-disclosure vital signs with interpretation results to a remote location, wherein the full-disclosure vital signs are real-time patient vital signs, by creating, at the portable patient monitor, data signals that includes a combination of bit-reduced/channel-reduced data signals and the uncompressed/unreduced data signals, wherein the uncompressed/unreduced data signals represent at least one of: the pathological event and emergency event; and synchronize verified interpretation results data with a data interpretation center and repository.

* * * * *